United States Patent
Li

(10) Patent No.: US 11,000,591 B2
(45) Date of Patent: May 11, 2021

(54) MULTIFUNCTIONAL TRADITIONAL CHINESE MEDICINE HEALTH PILLOW

(71) Applicant: Jisheng Li, Xingtai (CN)

(72) Inventor: Jisheng Li, Xingtai (CN)

( * ) Notice: Subject to any disclaimer, the term of this patent is extended or adjusted under 35 U.S.C. 154(b) by 0 days.

(21) Appl. No.: 16/549,067

(22) Filed: Aug. 23, 2019

(65) Prior Publication Data

US 2020/0138947 A1 May 7, 2020

Related U.S. Application Data

(63) Continuation of application No. PCT/CN2018/113313, filed on Nov. 1, 2018.

(51) Int. Cl.

| | | |
|---|---|---|
| *A61K 9/00* | (2006.01) |
| *A61K 41/00* | (2020.01) |
| *A61K 36/21* | (2006.01) |
| *A61K 36/716* | (2006.01) |
| *A61K 36/28* | (2006.01) |
| *A61K 36/258* | (2006.01) |
| *A61K 36/482* | (2006.01) |
| *A61K 36/704* | (2006.01) |
| *A61K 36/515* | (2006.01) |
| *A61K 36/488* | (2006.01) |
| *A61K 36/237* | (2006.01) |
| *A61K 36/8988* | (2006.01) |
| *A61K 36/232* | (2006.01) |
| *A61K 36/537* | (2006.01) |
| *A61K 36/48* | (2006.01) |
| *A61K 36/65* | (2006.01) |
| *A61K 36/66* | (2006.01) |
| *A61K 36/282* | (2006.01) |
| *A61K 36/185* | (2006.01) |
| *A61K 36/236* | (2006.01) |

(52) U.S. Cl.
CPC .......... *A61K 41/0004* (2013.01); *A61K 9/009* (2013.01); *A61K 36/185* (2013.01); *A61K 36/21* (2013.01); *A61K 36/232* (2013.01); *A61K 36/236* (2013.01); *A61K 36/237* (2013.01); *A61K 36/258* (2013.01); *A61K 36/28* (2013.01); *A61K 36/282* (2013.01); *A61K 36/48* (2013.01); *A61K 36/482* (2013.01); *A61K 36/488* (2013.01); *A61K 36/515* (2013.01); *A61K 36/537* (2013.01); *A61K 36/65* (2013.01); *A61K 36/66* (2013.01); *A61K 36/704* (2013.01); *A61K 36/716* (2013.01); *A61K 36/8988* (2013.01)

(58) Field of Classification Search
None
See application file for complete search history.

(56) References Cited

FOREIGN PATENT DOCUMENTS

| CN | 1178092 | * | 4/1998 |
| CN | 105455528 | * | 4/2016 |

* cited by examiner

*Primary Examiner* — Ralph J Gitomer
(74) *Attorney, Agent, or Firm* — HYIP

(57) ABSTRACT

The present invention discloses a multifunctional traditional Chinese medicine health pillow. The health pillow is in an inverted concave shape; an outermost layer is a dense old coarse cloth sheet. The health pillow of the present invention not only treats cervical spondylosis, but also can activate blood circulation to dissipate blood stasis, reconcile yin and yang, regulate pulmonary function, regulate blood pressure and reduce blood lipid, treat insomnia, forgetfulness and neurasthenia, conduct effective hypnosis and sleep aid, and is more widely used in adjunctive therapy of cervical vertebra syndrome, scapulohumeral periarthritis, ankylosing spondylitis, lumbar muscle strain, lumbar vertebrae hyperplasia, lumbar disc herniation, sciatica, multiple peripheral neuritis, rheumatic fibrositis, atrophic lateral sclerosis, pain caused by bone degenerative change and pain caused by various soft tissue injuries.

3 Claims, No Drawings

MULTIFUNCTIONAL TRADITIONAL CHINESE MEDICINE HEALTH PILLOW

TECHNICAL FIELD

The present invention relates to the field of modern traditional Chinese medicine comprehensive health devices, and more specifically, to a multifunctional traditional Chinese medicine health pillow.

BACKGROUND

At present, many varieties of health pillow products exist on the market, and have respective special characteristics. However, the health pillow products can be roughly classified into three categories. The first category is a variety of special-shaped pillows filled with high-elastic fiber space cotton and shaped according to the fillers. The first category is good in shape and comfort. However, cervical vertebra is only fixed and stabilized mechanically to alleviate the pain of the cervical vertebra without practical pharmaceutical effect. The second category is a health pillow filled with grain hulls or traditional Chinese medicine. The filling amount is single or small. The second category has certain curative effect, but the effect is poor. The third category is a wood appliance, i.e., a jade pillow. The magnet pillow is filled with traditional Chinese medicine. The third category has certain curative effect, but the shape arid the height of the pillow are fixed, which cannot satisfy the actual needs of free adjustment of the users. The three categories of pillows are all used for the treatment of cervical spondylosis, and have own pillow shapes; the contact surfaces are only limited to the cervical Vertebra position, and the pain and lesions of the shoulders, back, waist and buttocks cannot be considered.

SUMMARY

The purpose of the present invention is to overcome the defects of the prior art and provide a multifunctional traditional Chinese medicine health pillow.

The present invention is realized through the following solution:

A multifunctional traditional Chinese medicine health pillow is provided. The health pillow is in an inverted concave shape; an outermost layer is a dense old coarse cloth sheet; Chinese herbal medicine fillers are arranged in the old coarse cloth sheet; a plurality of pockets are arranged on the outer side of the old coarse cloth sheet; high-strength magnets are correspondingly arranged in the pockets.

According to the mass parts, the Chinese herbal medicine fillers comprise 60 parts of *Ligusticum chuanxiong* hort, 60 parts of *Achyranthes bidentata* Bl., 50 parts of *Clematis chinensis* Osbeck, 60 parts of *Siegesbeckia orientalis* L., 50 parts of *Panax pseudo-ginseng*, 30 parts of *Taxillus chinensis*(DC.) Danser., 30 parts of *Cinnamomum cassia* Presl, 50 parts of *Polygonum cuspidatum* Sieb. et Zucc., 40 parts of *Gentiana macrophylla*, 30 parts of *Pueraria lobata* (Willd.) Ohwi, 30 parts of *Notopterygium incisum* Ting ex H. T. Chang, 20 parts of *Gastrodia elata* Bl., 40 parts of *Angelica sinensis* (Oliv.) Diels, 60 parts of *Fallopia mulatiora* (Thunb.) Harald, 60 parts of *Salvia miltiorrhiza* Bge., 20 parts of *Cornus offieinalis* Sieb. et Zuec., 40 parts of *Spatholobus suberectus* Dunn, 30 parts of *Paeonia lactiflora* Pall., 35 parts of *Curcuma longa* L., 50 parts of *Cibotium barometz* (L.) J. Sm., 30 parts of *Carica papaya* L., 20 parts of *Ligusticum sinense* Oliv, 50 parts of *Fallopia multiflora* (Thunb.) Harald., 30 parts of *Eucommia ulmoides* Oliver, 30 parts of *Morus alba* L., 30 parts of *Heracleum hemsleyanum* Diels, 30 parts of *Paeonia lactiflora* Pall., 30 parts of *Ligustrum lucidum*, 15 parts of borneol, 20 parts of *Corydalis yanhusuo* (Y. H. Chou & Chun C. Hsu) W. T. Wang ex Z. Y. Su & C. Y. Wn, 15 parts of *Cyperus rotundus* L., 50 parts of *Dipsacales*, 15 parts of *Artemisia argyi* Levl. et Vant., 80 parts of *Davallia mariesii* Moore ex Bak., 30 parts of *Commiphora myrrha* Engl. and 80 parts of *Gynostemma pentaphyllum* (Thunb.) Makino.

Six pockets are symmetrically arranged.

The specifications of the dense old coarse cloth sheet are 200 cm in length and 80 cm in width; the specifications of the Chinese herbal medicine fillers are 150 cm in length, 75 cm in width and 2 cm in, thickness; and the specifications of the high-strength magnets are 15 cm in length, 10 cm in width and 2.5 cm in height.

The present invention has the beneficial effects: the health pillow of the present invention not only can satisfy the need of the patients for adjusting the height and the width of the pillow at any time, but also can realize full and close contact of the cervical vertebra, shoulders, back, waist and buttocks with the medicine to the largest degree, and adopts a pure pollution-free old coarse cloth made of purified cotton to ensure more air permeability and health. The greatest breakthrough of the product is: the health pillow of the present invention not only treats cervical spondylosis, but also can activate blood circulation to dissipate blood stasis, reconcile yin and yang, regulate pulmonary function, regulate blood pressure and reduce blood lipid, treat insomnia, forgetfulness and neurasthenia, conduct, effective hypnosis and sleep, aid, and is more widely used in adjunctive therapy of cervical vertebra syndrome, scapulohumeral periarthritis, ankylosing spondylitis, lumbar muscle strain, lumbar vertebrae hyperplasia, lumbar disc herniation, sciatica, multiple peripheral neuritis, rheumatic fibrositis, atrophic lateral sclerosis, pain caused by bone degenerative change and pain caused by various soft tissue injuries. The health pillow can also treat some involuntary pains with unknown causes and uncertain positions, inhibit a variety of pathogenic bacteria and treat and prevent skin diseases.

DETAILED DESCRIPTION

The present invention will be further described below in combination with specific embodiments.

A multifunctional traditional Chinese medicine health pillow is provided. The health pillow is in an inverted concave shape; an outermost layer is a dense old coarse cloth sheet; Chinese herbal medicine fillers are arranged in the old coarse cloth sheet; a plurality of pockets are arranged on the outer side of the old coarse cloth sheet; high-strength magnets are correspondingly arranged in the pockets.

According to the mass parts, the Chinese herbal medicine fillers comprise 60 parts of *Ligusticum chuanxiong* hort, 60 parts of *Achyranthes bidentata* Bl., 50 parts of *Clematis chinensis* Osbeck, 60 parts of *Siegesbeckia orientalis* L., 50 parts of *Panax pseudo-ginseng*, 30 parts of *Taxillus chinensis* (DC.) Danser., 30 parts of *Cinnamomum cassia* Presl, 50 parts of *Polygonum cuspidatum* Sieb. et Zucc., 40 parts of *Gentiana macrophylla*, 30 parts of *Pueraria lobata* (Willd.) Ohwi, 30 parts of *Notopterygium incisum* Ting ex H. T. Chang, 20 parts of *Gastrodia elata* Bl., 40 parts of *Angelica sinensis* (Oliv.) Diels, 60 parts of *Fallopia multiflora* (Thunb.) Harald., 60 parts of *Salvia miltiorrhiza* Bge., 20 parts of *Cornus offieinalis* Sieb. et Zucc., 40 parts of *Spatholobus suberectus* Dunn, 30 parts of *Paeonia lactiflora*

Pall., 35 parts of *Curcuma longa* L., 50 parts of *Cibotium barometz* (L.) J. Sm., 30 parts of *Carica papaya* 20 parts of *Ligusticum sinense* Oliv, 50 parts of *Fallopia multiflora* (Thunb.) Harald., 30 parts of *Eucommia ulmoides* Oliver, 30 parts of *Morus alba* L., 30 parts of *Heracleum hemsleyanum Diels,* 30 parts of *Paeonia lactiflora* Pall., 30 parts of *Ligustrum lucidum,* 15 parts of borneol, 20 parts of *Corydalis yanhusuo* (Y. H. Chou & Chun C. Hsu) W. T. Wang ex Z. Y. Su C. Y. Wu, 15 parts of *Cyperus rotundus* L., 50 parts of *Dipsacales,* 15 parts of *Artemisia argyi* Levl. et Vant., 80 parts of *Davallia mariesii* Moore ex Bak., 30 parts of *Commiphora myrrha* Engl. and 80 parts of *Gynostemma pentaphyllum* (Thunb.) Makino.

Six pockets are symmetrically arranged. The specifications of the dense old coarse cloth sheet are 200 cm in length and 80 cm in width; the specifications of the Chinese herbal medicine fillers are 150 cm in length, 75 cm in width and 2 cm in thickness; and the specifications of the high-strength magnets are 15 cm in length, 10 cm in width and 2.5 cm in height. In practical application, the dense old coarse cloth sheet prevents medicinal powder from falling everywhere.

The cloth for the Chinese herbal medicine fillers can be slightly thin, which is favorable for volatilization and application of medical particles. The Chinese herbal medicine fillers are put flatwise on the dense old coarse cloth sheet so that the contact between the medicine and the skin is not influenced during folding and turning.

The technical solution of the present application will be further described below in combination with specific embodiments.

The numbers (see the digitals in front of names of traditional Chinese medicine) and dosages of various traditional Chinese medicine components in the Chinese herbal medicine fillers of the present application are shown in Table 1.

TABLE 1

Traditional Chinese Medicine Components in Chinese Herbal Medicine Fillers

| 1 | 2 | 3 | 4 | 5 | 6 |
|---|---|---|---|---|---|
| *Ligusticum chuanxiong hort* 60 g | *Achyranthes bidentata* Bl. 60 g | *Clematis chinensis* Osbeck 50 g | *Siegesbeckia orientalis* L. 60 g | *Panax pseudo-ginseng* 50 g | *Taxillus chinensis*(DC.) Danser. 30 g |
| 7 | 8 | 9 | 10 | 11 | 12 |
| *Cinnamomum cassia* Presl 30g | *Polygonum cuspidatum* Sieb.et Zucc. 50 g | *Gentiana macrophylla* 40 g | *Pueraria lobata* (Willd.) Ohwi 30 g | *Notopterygium incisum* Ting ex H.T. Chang 30 g | *Gastrodia elata* Bl. 20 g |
| 13 | 14 | 15 | 16 | 17 | 18 |
| *Angelica sinensis* (Oliv.) Diels 40 g | *Fallopia multiflora* (Thunb.) Harald 60 g | *Salvia miltiorrhiza* Bge. 60 g | *Cornus officinalis* Sieb. et Zucc. 20 g | Spatholobus suberectus Dunn 40 g | *Paeonia lactiflora* Pall. 30 g |
| 19 | 20 | 21 | 22 | 23 | 24 |
| *Curcuma longa* L. 35 g | *Cibotium barometz* (L.) J.Sm. 50 g | *Carica papaya* L. 30 g | *Ligusticum sinense* Oliv. 20 g | *Fallopia multiflora* (Thunb.) Harald. 50 g | *Eucommia ulmoides* Oliver 30 g |
| 25 | 26 | 27 | 28 | 29 | 30 |
| *Morus alba* L. 30 g | *Heracleum hemsleyanum* Diels 30 g | *Paeonia lactiflora* Pall 30 g | *Ligustrum lucidum* 30 g | borneol 15 g | *Corydalis yanhusua* (Y.H. Chou & Chun C.Hsu) W.T.Wang ex C.Y.Wu 20 g |
| 31 | 32 | 33 | 34 | 35 | 36 |
| *Cyperus rotundas* L. 15 g | *Dipsacales* 50 g | *Artemisia argyi* Levl.et Vant. 15 g | *Davallia mariesii* Moore ex Bak 80 g | *Commiphora myrrha* Engl. 30 g | *Gynostemma pentaphyllum* (Thunb.) Makino 80 g |

The pharmaceutical effects of various traditional Chinese, medicine components in the present application are shown in the pharmacopoeia, and the synergistic effects of the various traditional Chinese medicine components in the present application are as follows.

1, 2, 3, 5, 8, 9, 11, 15 17, 19, 20, 23, 25, 26, 29 and 36 are sovereign drugs for facilitating walking, and can dredge tendons and muscles, activate blood circulation to dissipate blood stasis, dispel cold and remove dampness, resist inflammation and relieve spasm.

2, 15 32, 34 and 35 can fill the physique and promote the secondary development of skeletal tissue.

7 *Cinnamomum cassia* Presl has a specific hyperemia effect and has the effect of strengthening other drugs of activating blood circulation to dissipate blood stasis.

8 *Polygonum cuspidatum* Sieb. et Zucc. has the effects of promoting blood circulation, eliminating phlegm, alleviating cough and asthma, resisting arrhythmia, and clearing heat and removing toxicity.

9 *Gentiana macrophylla* is bitter but not dry, is acrid in taste to disperse inevitably, and is a moisturizer in the wind medicine. It can dispel wind and overcome dampness, relax and activate the tendons, promote joint movement, promote blood circulation to arrest pain, mainly treat involuntary pains and resist allergy.

1, 3, 4, 5, 9, 11, 13, 14, 15, 16, 19, 20, 21, 23, 25, 27, 28, 32, 33 and 36 resist bacteria, resist inflammation, resist viruses, resist, aging, resist tumors, resist allergy, can inhibit *Mycobacterium tuberculosis* dermatophyte, anti-pathogenic microorganisms, various pathogenic bacteria, dysentery bacteria and *Staphylococcus aureus* toxoids, and treat and prevent skin diseases, infectious diseases, rubella, eczema, ulcerative carbuncle and acariasis.

2, 4, 5, 14, 15, 18, 21, 24, 27, 28, 32, 35 and 36 mainly improve immunity and resist aging.

1, 2, 4, 5, 6, 12, 13, 14, 26 and 28 improve microcirculation, increase blood flow, inhibit platelet aggregation, resist thrombosis and resist atherosclerosis.

1, 2, 3, 5, 7, 12, 13, 15, 23, 24 and 26 are sedative, analgesic, antiinflammatory and anticonvulsant drugs, and can conduct hypnosis and sleep aid.

11, 13, 14, 15 and 26 treat neurasthenia, insomnia and forgetfulness, treat vertigo, tonify the liver and kidney, benefit blood and essence, nourish blood and protect the liver.

1, 7, 9, 11, 13, 18, 19, 22, 26, 27, 28, 30, 31, 32, 33 and 35 contain various volatile oil and various acids, and have strong permeability.

1 and 25 are Qi medicine in the blood, promote walking, carry other drugs to the top of the head, promote four limbs, circumscribe the fur and bypass the muscles.

29 borneol reduces myocardial oxygen consumption, prolongs anti-hypoxia time, resists myocardial infarction, has certain pain relief and mild antiseptic effects, and especially can increase the concentration of drugs in the brain through, blood and brain disorders.

2, 3, 5, 6, 10, 12, 13, 14, 19, 22, 24, 27, 28, 30 and 36 mainly decrease blood pressure, reduce blood lipid and reduce blood glucose.

13, 14, 18, 21, 30 and 36 relieve internal heat or fever, loosen bowel to relieve constipation, dispel dampness, harmonize the stomach, regulate gastric acid secretion, treat indigestion and resist gastric ulcer and neoplasm.

32 *Dipsacales* [fried] is rich in vitamin E, resists vitamin E deficiency, regulates the secretion of sex hormones, supplements vitamin E, rehabilitates the fetus, restores energy, enriches and strengthens essence, and effectively alleviates menopausal syndrome.

33 *Artemisia argyi* Levl. et Vat. and 36 *Gynostemma pentaphylla* alleviate cough and eliminate phlegm and asthma.

34 *Davallia mariesii* Moore ex Bak. has the effect of stimulating cell compensatory hyperplasia on osteoarticular cartilage, can partially improve the degenerative disease of bone joint due to the change of the mechanical application line, can reduce the disease rate of the bone joint, and has specific effect on inflammation and damage of the bone joint.

36 *Gynostemma pentaphylla* regulates blood pressure in two directions, reduces blood lipid and blood glucose, resists cancer and tumors, resists fatigue and aging, promotes sleep, regulates the central nervous system in two directions, enhances body immunity and regulates human physiological functions.

The health pillow of the present application comprises 36 kinds of Chinese herbal medicine fillers with natural plants. Each kind has multiple effects, interacts to jointly revise and care the health of patients, and, simultaneously performs respective medical characteristics. According to the effects, the following discrimination can be made. 16 kinds of Chinese herbal medicine contain volatile oil; 16 kinds of Chinese herbal medicine can promote walking; 16 kinds of Chinese herbal medicine can resist bacteria, viruses, aging and tumors; and 10 kinds of Chinese herbal medicine regulate immunity, etc. The fillers are rich in hundreds of beneficial substances, use the characteristics of smell immersion and fat infiltration for magnetization by strong magnetism, and enable drug molecules to have activity, adhesion and strong penetrability. These medicines magnetized by strong magnetism penetrate into the skin and enter the blood circulation system, reconstruct dislocation, relax the muscles, dredge tendons, activate blood circulation to dissipate blood stasis, resist bacteria, and remove inflammation and pain. The medicine particles enter the respiratory system with breathing, resuscitate with aromatics, reconcile yin and yang, regulate pulmonary function, and perform the effects of stabilizing the cervical spine and vertebra by the medicine pillow, as well as medicine stimulation, mental regulation and high magnetic field effects. The health pillow comprehensively acts on the disease part of the patient body to treat inflammatory lesions of cervical vertebrae, thoracic vertebrae, lumbar vertebrae sacral vertebra and coccygeal vertebrae, maintain the safety of the whole, vertebra body, effectively relieve pain and complications, treat the skin problem, simultaneously regulate and decrease blood pressure, reduce blood lipid, reduce blood glucose, regulate and enhance immune functions of the organisms, treat insomnia, forgetfulness and neurasthenia, effectively conduct hypnosis and sleep aid and improve sleep quality.

The health pillow of the present application is designed into an inverted concave shape; and six pockets are arranged at the Chinese herbal medicine fillers and used for putting two strong magnets. The pillow can be folded and rolled up. After folded, the pillow can be used as a backrest of neck, shoulder and back and is equivalent to a large pillow which is capacious enough. The human shoulder and back lie flat on the pillow. After rolled up into a cylinder shape and cushioned on the cervical vertebra position behind the head, the pillow can be used as a dedicated cervical vertebra pillow. The medicine pillow extends to act as a mattress which can be varied at random and suitable for multiple demands. During folding, the pillow is rolled up and both ends are naturally high in a shape of a shoe-shaped gold ingot. The pillow has a thickness of a fist, and is fitted with the height of cervical vertebra to play the effects of stabilizing cervical vertebra and fixing cervical vertebra and avoid damaging, cervical vertebra due to incorrect postures in sleep or rest. With the cushion of the strong magnets, the pillow has a special efficacy that both ends are high. The pillow cushion extends to act as the mattress, so that an inverted concave half-round cut is seen. Considering s curve of the human body, in lying down, the hips are protruding, the waist is suspended, the lumbar vertebrae are still under pressure, and the lumbar vertebrae do not get a rest. The human body is easy to fatigue, but after deletion, the waist is not suspended. The full contact between the body and the medicine is maximized, which is beneficial to medicine absorption. There is no any pressure on the waist. The human body is more comfortable, and the lumbar vertebra can be effectively protected. At the same time, the pressure of the coccygeal vertebrae can also be relieved; stabilization, and fixation protection effects are performed on the entire vertebra body; blood circulation is smooth; and the central nervous system is protected.

It should be added that the health pillow has a length of 150 cm and is already long enough. Another use of this design is that for patients with short stature or shortened or deformed body due to some reasons, when using the medicine pillow, a part of the medicine pillow can be rolled up from above to below to act as a cervical vertebra pillow, and the gap of the lower part of the medicine pillow cushion can still serve the lumbar vertebra, the coccygeal vertebrae and the ischial bone without being affected.

During the use of the medicine pillow, the human body lies on the medicine pillow cushion, just like being, in a semi-closed small environment. The whole body is immersed in the medicine at every moment, with the medicine entering the heart, spleen and the bone. A small circular cycle is repeated, and the pharmaceutical effect is remarkable and lasting.

In the actual preparation of the Chinese herbal medicine fillers, 36 kinds of dried Chinese herbal medicine can be pre-configured according to a prescription, mixed together, and pulverized into medium-thick powder. Then, a health pillowcase made of old coarse cloth is laid flat, and space cotton is about 1.5 cm thick on the top. The medicine powder is evenly spread on the space cotton, and then a layer of sterile medical gauze is covered on the space cotton. Then, the health pillowcase is rolled up from the lower gap, which is similar to rolling a quilt. When the health pillowcase is rolled up in the end, the health pillowcase is gently pulled. The whole health pillow is completely filled, sealed and sewn vertically and horizontally with a large stitch method finely and densely, with a row spacing of 1.5 cm. At this point, the Chinese herbal, medicine fillers of the health pillow are manufactured. This manufacturing has the following advantages.

A: The sweat absorption and comfort of the health pillow are ensured; foreign body sensations of the neck, shoulder, back, waist buttocks and four limbs of the body are relieved; and fatigue is resisted.

B: The medicine uses the space cotton as a cushion bracket, is uniformly attached to the space cotton and is fixed by a small square space, so that the pillow cushion may not be gathered together due to being folded and turned.

C: The space cotton has high elasticity and air permeability, and is mixed with the medicinal powder. Each square is, a medicinal airbag. When the space cotton is pressed by a human body, the human body naturally breathes to exhale the medicinal powder and smell ad inhale fresh air. The human body is immersed and penetrated by the medicine, which is favorable for medicinal absorption.

D: The health pillow cushion can be dried under sunshine, which is favorable for sterilizing and preventing invasion of mites and various bacteria, is more healthy and is also favorable for restoring the elasticity of the pillow cushion. It should be noted to prohibit exposure to the sun, watering on the pillow cushion, washing, raining and other practices of destroying the pillow cushion.

As an important part of the present application, the high-strength magnets are independent of the health pillow, are attached to the health pillow and are determined to preserved or peeled off depending on the actual situation of a patient.

1. Frail old persons, children and pregnant women are not suggested to use the health pillow with the high-strength magnets.

2. It is recommended to take out the high-strength magnets from patients with metal components in the body.

3. It is recommended to take out the high-strength magnets from patients with radiation sources or mobile phones.

4. It is recommended to take out the high-strength magnets from patients who show palpitation, dizziness, nausea, night sweats, or severe headache during the use of the medicine pillow.

The high-strength magnets have a sedative effect on the central nervous system and have a blood-supplying effect on iron deficiency anemia. Magnetism has the effects of activating cell energy, promoting blood circulation, removing free radicals from blood vessel walls, reducing blood viscosity, reducing blood lipid, tranquilizing and allaying excitement, reducing inflammation and swelling, relieving pain and diarrhea, improving organism immunity and resisting aging. The magnetized medicine particles volatilize oil, have more vitality and adhesion, have more transmission power, strengthen the pharmaceutical effect, also effectively slowly release the pharmaceutical effect and prolong the service life of the medicine pillow. The effective period of a general medicine pillow is about half a year. After the, high-strength magnets are added for magnetization, the health pillow is successfully extended to the effective use period of more than one year to one and, a half years. The high-strength magnets can be freely selected according to the actual needs of the patients, and can be put into the pockets at random, and then fixedly used.

Although the technical solutions of the present invention are explained and enumerated in detail, it should be understood that those skilled in the art will make modifications to the above embodiments or adopt equivalent alternative solutions, which is apparent to those skilled in the art. These modifications or improvements made without departing from the spirit of the present invention belong to the protection scope of the present invention.

The invention claimed is:

1. A traditional Chinese medicine health pillow, comprising:
    an outermost layer made of coarse cloth sheet;
    Chinese herbal medicine fillers arranged in the coarse cloth sheet;
    a plurality of pockets arranged on the outer side of the coarse cloth sheet; and
    a plurality of magnets correspondingly arranged in the pockets;
    the Chinese herbal medicine fillers comprise, according to the mass parts,
    60 parts of *Ligusticum chuanxiong* hort,
    60 parts of *Achyranthes bidentata* Bl.,
    50 parts of *Clematis chinensis* Osbeck,
    60 parts of *Siegesbeckia orientalis* L.,
    50 parts of *Panax pseudo-ginseng*,
    30 parts of *Taxillus chinensis* (DC.)Danser,
    30 parts of *Cinnamomum cassia* Presl, 50 parts of *Polygonum cuspidatum* Sieb. et Zucc.,
40 parts of *Gentiana macrophylla*,
30 parts of *Pueraria lobata* (Willd.) Ohwi,
30 parts of *Notopterygium incisum* Ting ex H. T. Chang,
20 parts of *Gastrodia elata* Bl.,
40 parts of *Angelica sinensis* (Oliv.) Diel,
60 parts of *Fallopia multiflora* (Thunb.) Harald,
60 parts of *Salvia miltiorrhiza* Bge.,
20 parts of *Cornus officinalis* Sieb. et Zucc.,
40 parts of *Spatholobus suberectus* Dunn,
30 parts of *Paeonia lactiflora* Pall,
35 parts of *Curcuma longa* L.,
50 parts of *Cibotium barometz* (L.) J. Sm.,
30 parts of *Carica papaya* L.,
20 parts of *Ligusticum sinense* Oliv.,
50 parts of *Fallopia multiflora* (Thunb.) Harald.,
30 parts of *Eucommia ulmoides* Oliver,
30 parts of *Morus alba* L.,
30 parts of *Heracleum hemsleyanum* Diel,
30 parts of *Paeonia lactiflora* Pall.,
30 parts of *Ligustrum lucidum*,
15 parts of borneol,
20 parts of *Corydalis yanhusuo* (Y. H. Chou & Chun C. Hsu) W. T. Wang ex Z. Y. Su & C. Y. Wu,
15 parts of *Cyperus rotundas* L.,
50 parts of *Dipsacales*,
15 parts of *Artemisia argyi* Levl. et Vant.,
80 parts of *Davallia mariesii* Moore ex Bak.,
30 parts of *Commiphora myrrha* Engl. and
80 parts of *Gynostemma pentaphyllum* (Thunb.) Makino.

2. The traditional Chinese medicine health pillow of claim 1, wherein the total number of the plurality of pockets is six and the six pockets are symmetrically arranged.

3. The traditional Chinese medicine health pillow of claim 1, wherein the coarse cloth sheet is 200 cm in length and 80 cm in width; the Chinese herbal medicine fillers are 150 cm in length, 75 cm in width and 2 cm in thickness; and the magnets are 15 cm in length, 10 cm in width and 2.5 cm in height.

\* \* \* \* \*